United States Patent
Son

(10) Patent No.: US 8,350,571 B2
(45) Date of Patent: Jan. 8, 2013

(54) ELECTRONIC SALT METER

(76) Inventor: Yun-Ho Son, Seoul (KR)

( * ) Notice: Subject to any disclaimer, the term of this patent is extended or adjusted under 35 U.S.C. 154(b) by 247 days.

(21) Appl. No.: 12/875,257

(22) Filed: Sep. 3, 2010

(65) Prior Publication Data

US 2011/0140704 A1 Jun. 16, 2011

(30) Foreign Application Priority Data

Sep. 7, 2009 (KR) ........................ 10-2009-0084191

(51) Int. Cl.
*G01N 27/02* (2006.01)

(52) U.S. Cl. ........ 324/441; 324/693; 324/721; 324/722; 324/724; 137/79; 210/767; 210/746; 73/61.41; 73/73; 374/10

(58) Field of Classification Search .................. 324/441, 324/76.11, 722, 721, 685, 693, 724; 374/10; 700/299; 137/79; 73/73, 61.41; 210/767, 210/746
See application file for complete search history.

(56) References Cited

U.S. PATENT DOCUMENTS

| 3,748,899 | A | * | 7/1973 | Gregg et al. | ............. | 73/170.34 |
| 4,823,087 | A | * | 4/1989 | Sugimori | ............. | 324/441 |
| 2009/0213097 | A1 | * | 8/2009 | Lin | ............. | 345/204 |
| 2009/0242493 | A1 | * | 10/2009 | Samborn et al. | ............. | 210/767 |

* cited by examiner

*Primary Examiner* — Huy Q Phan
*Assistant Examiner* — Thang Le
(74) *Attorney, Agent, or Firm* — Design IP

(57) ABSTRACT

An electronic salt meter including a sensor rod, salt meter body and receiving components to measure a temperature and salinity. The electronic salt meter includes a first and sensor electrode and a temperature sensor to detect a temperature of the measurement object. A measurement monitoring unit detects whether the first and second sensor electrodes are electrically connected to each other. A salinity measurement unit applies an AC power to the first and second sensor electrodes to measure salinity of the measurement object. A temperature measurement unit applies a power to the temperature sensor to measure the temperature of the measurement object. A thermal equilibrium detection unit stores the temperature value previously measured, and when the temperature variation is less than a predetermined threshold, it is determined as a thermal equilibrium state. A room-temperature salinity conversion unit converts the salinity value into a salinity value at room temperature.

6 Claims, 5 Drawing Sheets

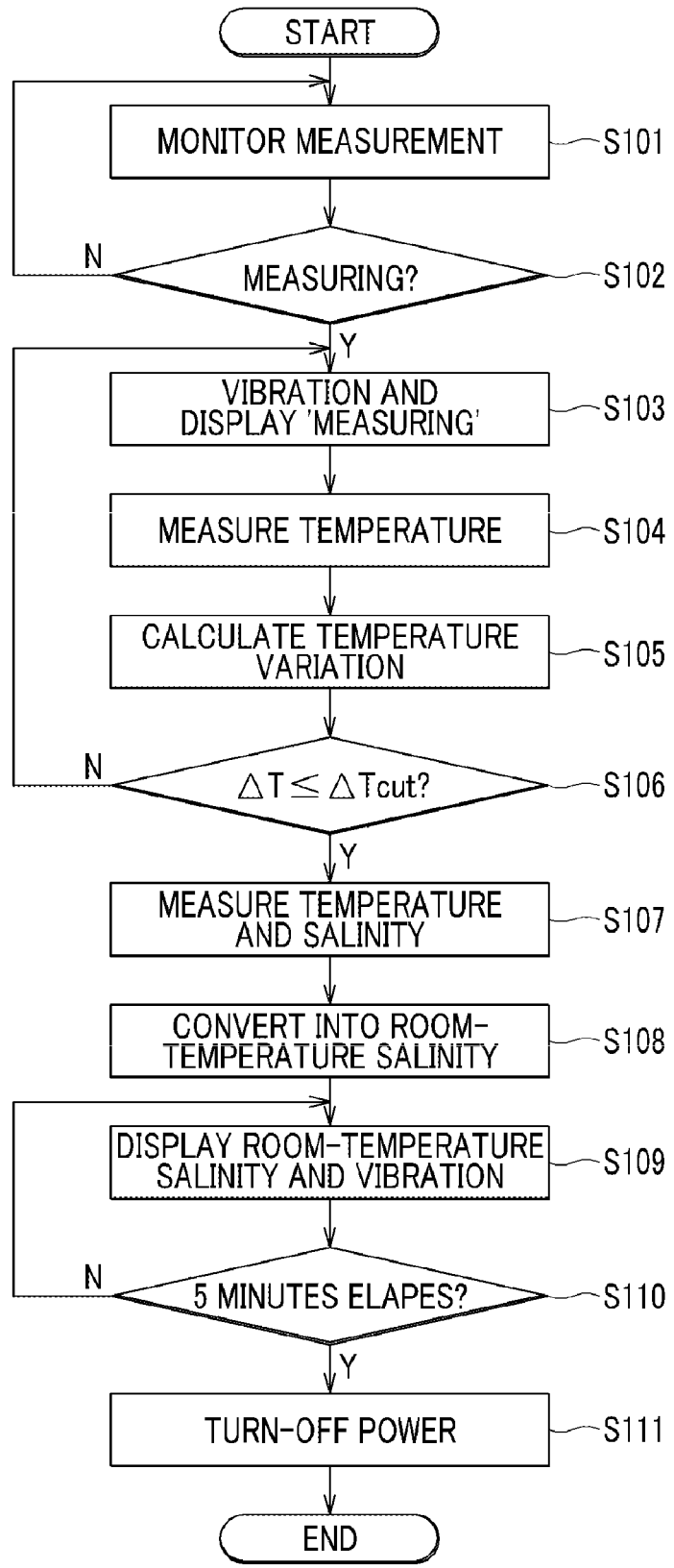

ELECTRONIC SALT METER

BACKGROUND OF THE INVENTION

1. Field of the Invention

The present invention relates to an electronic salt meter, and more particularly, to an electronic salt meter in which a temperature sensor quickly reaches thermal equilibrium with a measurement object to quickly and accurately measure a temperature, and a power is automatically turned on when measured to improve use convenience by removing various buttons.

2. Description of the Related Art

Recently, as attention regarding well-being and health has increased, the interest in a salt meter for measuring salinity contained in foods is increasing because salty foods are discovered as one of main factors causing a high blood pressure.

A conductivity method, which uses a conductivity difference depending on an amount of salinity contained in an object to be measured (hereinafter, referred to as a measurement object) and a reflectometer method, which uses a light refraction difference depending on the amount of salinity contained in the measurement object are widely known as a method for measuring salinity of a measurement object such as foods or sea water.

The conductivity method is a method in which conductivity due to ionized salinity (electrolyte) melting in the measurement object is measured using current flowing between two electrodes. Here, the salinity has an influence on a temperature. Typically, it is known that the salinity is changed by about 2% as the temperature is changed by about 1° C.

Thus, it is important that the temperature is precisely measured to precisely measure the salinity. Also, for avoiding user's confusion, the salinity of the measurement object is unified as salinity (unit, %, or ppt) at room temperature (25° C.), and then, the unified salinity is displayed. Thus, it is necessary that salinity measured at different temperatures is converted into salinity at room temperature.

SUMMARY OF THE INVENTION

Accordingly, the present invention is directed to an electronic salt meter that substantially obviates one or more problems due to limitations and disadvantages of the related art.

Since salinity is changed by a temperature, it is very important that an actual temperature of a measurement object is precisely measured to precisely measure salinity when salinity of the measurement object is measured.

However, according to a related art electronic salt meter that measures salinity using a conductivity method, there is a limitation that accuracy of measured salinity is low when salinity is measured because it is difficult to precisely measure the actual temperature of the measurement object. That is, according to the related art electronic salt meter, it takes a long time (e.g., about 2 minutes or more) for which a temperature of a portion of a temperature measurement sensor is diffused into a sensor rod to reach temperature equilibrium between the temperature sensor and the sensor rod. Thus, the measurement time is longer, and the accuracy is lower.

Also, since the related art electronic salt meter includes manipulation buttons for performing an ON/OFF operation of a power or controlling the measurement, it is difficult to realize waterproof of water-tight construction of a measurement unit.

An object of the present invention is to provide an electronic salt meter in which a temperature sensor and a measurement object quickly reach temperature equilibrium to measure a temperature and salinity in a thermal equilibrium state, thereby improving a measurement speed and accuracy.

Another object of the present invention is to provide an electronic salt meter in which whether a measurement operation is preformed is monitored in a power save mode, and when contact with a measurement object is detected, since a power is automatically turned on and the electronic salt meter is converted into a normal mode, a power button or measurement buttons are not required to improve use convenience and realize waterproof of water-tight construction.

According to an aspect of the present invention, there is provided an electronic salt meter including: a sensor rod configured to easily contact a measurement object; a first sensor electrode protruding from a tip of the sensor rod to apply a voltage to the measurement object; a second sensor electrode disposed on the tip of the sensor rod to apply the voltage to the measurement object; a temperature sensor built in the first sensor electrode to detect a temperature of the measurement object; a body case coupled to the sensor rod, the body case having a space in which components are received; a power source unit outputting an ordinary power in a power save mode during ordinary times and outputting a measurement power for normally operating a circuit during the measurement; a measurement monitoring unit operated by the ordinary power to detect measurement state according to whether the first and second sensor electrodes are electrically connected to each other; a salinity measurement unit applying an AC power to the first sensor electrode and the second sensor electrode to measure salinity of the measurement object using a conductivity method; a temperature measurement unit applying the power to the temperature sensor to measure the temperature of the measurement object; a thermal equilibrium detection unit storing a temperature value previously measured by the temperature measurement unit with a predetermined time interval after the measurement starts according to a control signal and comparing a current temperature with a previous temperature to obtain a temperature variation, and then, when the temperature variation is less than a predetermined threshold, it is determined as a thermal equilibrium state to command actual measurement to the salinity measurement unit and the temperature measurement unit; a room-temperature salinity conversion unit converting the salinity value measured by the salinity measurement unit into a salinity value at room temperature using the temperature measured by the temperature measurement unit and the salinity value measured by the salinity measurement; a display unit displaying an operation state and the salinity value; and a control unit controlling display unit to display a letter 'measuring' on the display unit when the measurement start is detected through the measurement monitoring unit and to receive the salinity value at room temperature from the room-temperature salinity conversion unit, thereby displaying the salinity value at room temperature on the display unit when the thermal equilibrium state is reached while monitoring the thermal equilibrium state through the thermal equilibrium detection unit.

BRIEF DESCRIPTION OF THE DRAWINGS

FIG. 6 is a flowchart illustrating an operation process of an electronic salt meter according to the present invention.

DETAILED DESCRIPTION OF THE INVENTION

Technical objectives of the present invention will become evident through the following embodiments. The following embodiments are merely illustrative of the present invention, and thus, this should not be construed as limited to the scope of the present invention.

Figure 1:
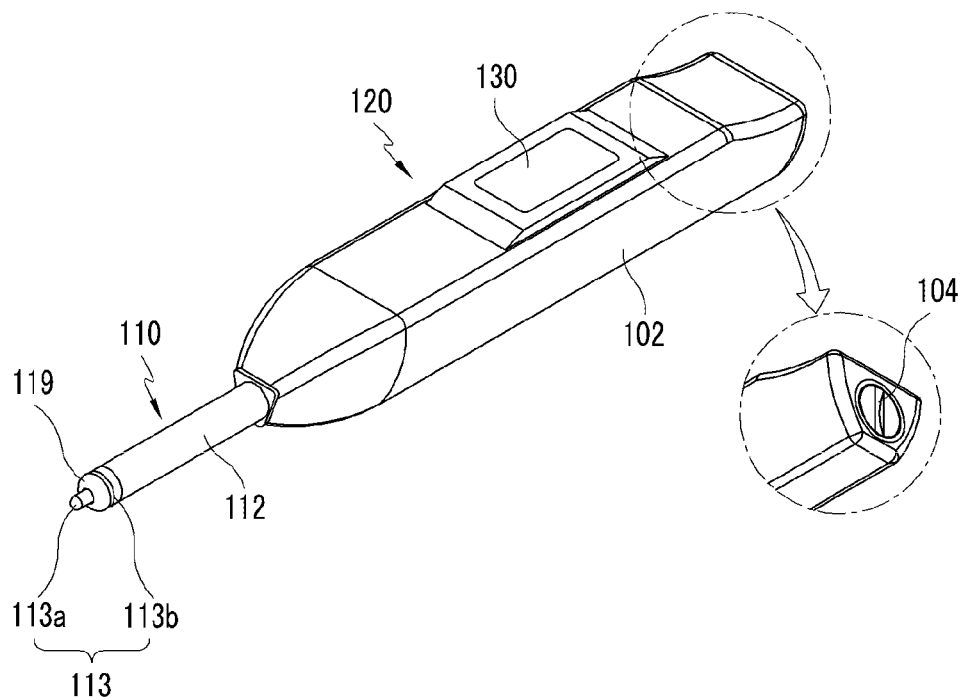
FIG. 1 is a perspective view of an electronic salt meter according to the present invention.
Figure 2:
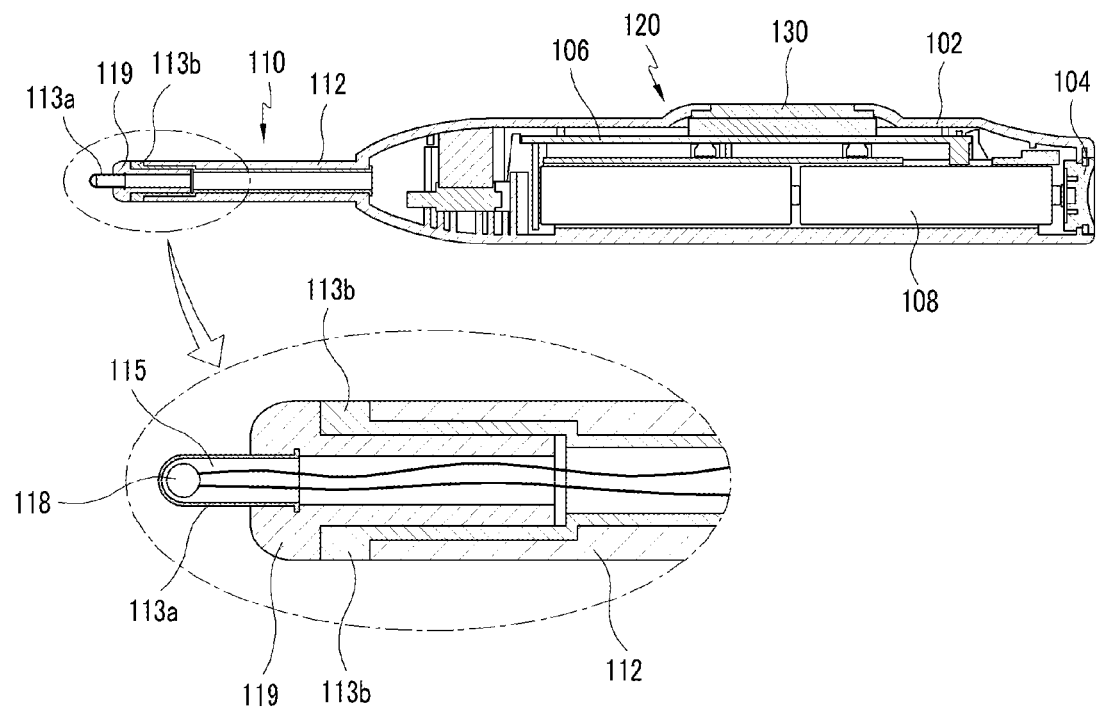
FIG. 2 is a side-sectional view illustrating the electronic salt meter of FIG. 1.
Figure 3:
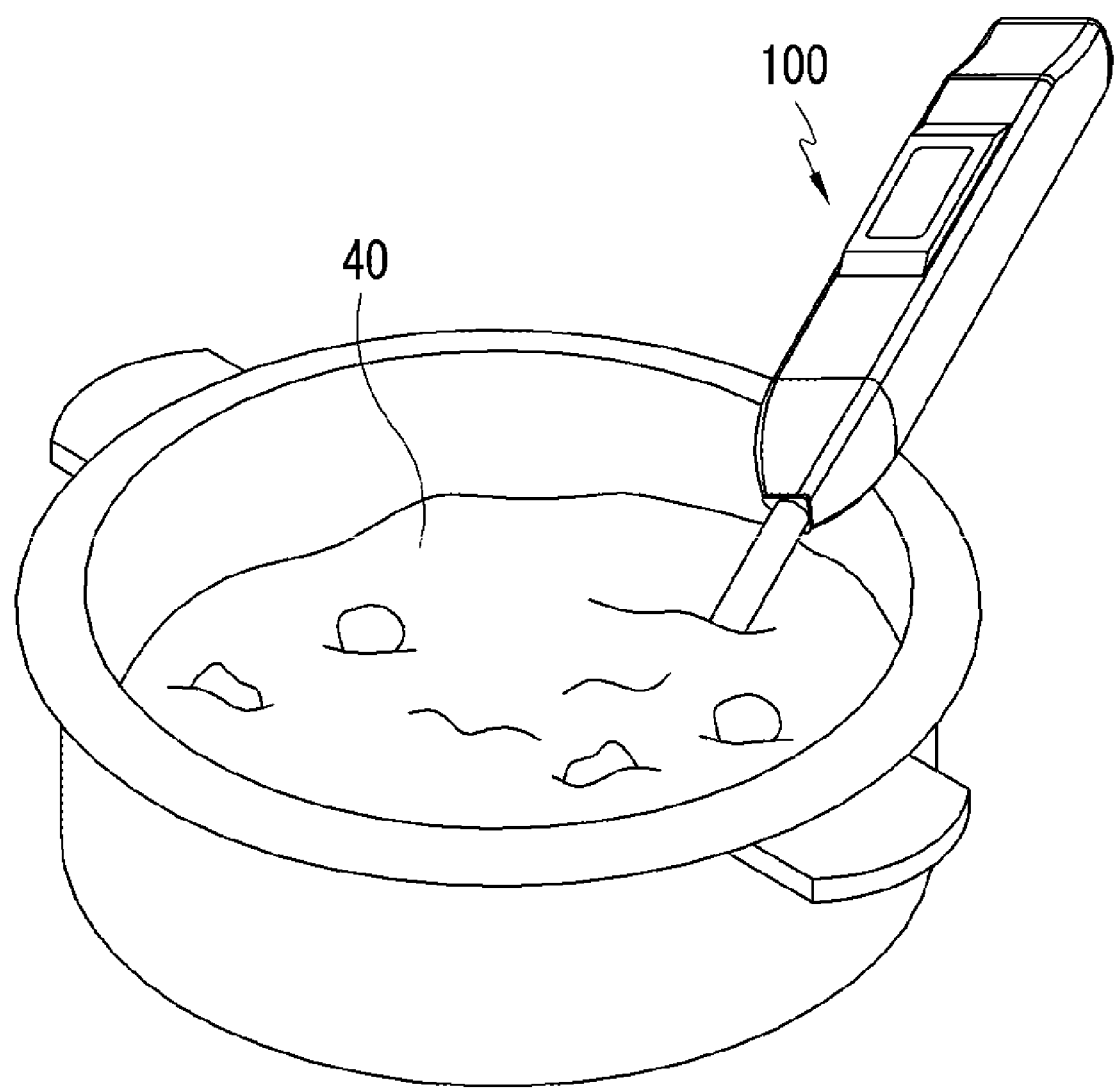
FIG. 3 is a schematic view illustrating a use status of an electronic salt meter according to the present invention.

FIG. 1 is a perspective view of an electronic salt meter according to the present invention, FIG. 2 is a side-sectional view illustrating the electronic salt meter of FIG. 1, and FIG. 3 is a schematic view illustrating a use status of an electronic salt meter according to the present invention.

Referring to FIGS. 1 to 3, an electronic salt meter 100 according to the present invention includes a sensor rod 110, which is insertable into an object 20 to be measured (hereinafter, referred to as a measurement object 20) and a salt meter body 120, which measures a temperature and salinity of the measurement object 20 to display the measured values as a salinity at room temperature (25° C.). The sensor rod 110 and the salt meter body 120 may be integrally coupled to each other.

The sensor rod 110 includes a pair of electrodes, which are arranged in a front-rear direction to measure salinity. The pair of electrodes includes a first sensor electrode 113a protruding from a tip of a rod body 112 and a second sensor electrode 113b. The first sensor electrode 113a and the second sensor electrode 113b are disposed with an insulator 119 therebetween. A temperature sensor 118 for detecting a temperature is built in the first sensor electrode 113a disposed on the tip of the sensor rod 110. A thermal cream 115 is filled in the first sensor electrode 113a to efficiently transmit heat of the first sensor electrode 113a into the temperature sensor 118. Thus, the temperature sensor 118 used in the present invention may quickly receive the heat by the thermal cream 115 when measured, and simultaneously, prevent the heat from being lost toward the rod body 112 by the insulator (e.g., plastic) 119 to very quickly obtain temperature equilibrium between the temperature sensor 118 and the measurement object 20.

The salt meter body 120 includes a case 102 having a cylindrical shape, in which the inside thereof is empty to receive a printed circuit board (PCB) 106 and a battery 108. Also, a display unit 130 is attached to the case 102. A dry battery cap 104 is coupled to an end of the case 102. Since the electronic salt meter 100 has an automatic-on function, buttons for power control and measurement are not required.

Figure 4:
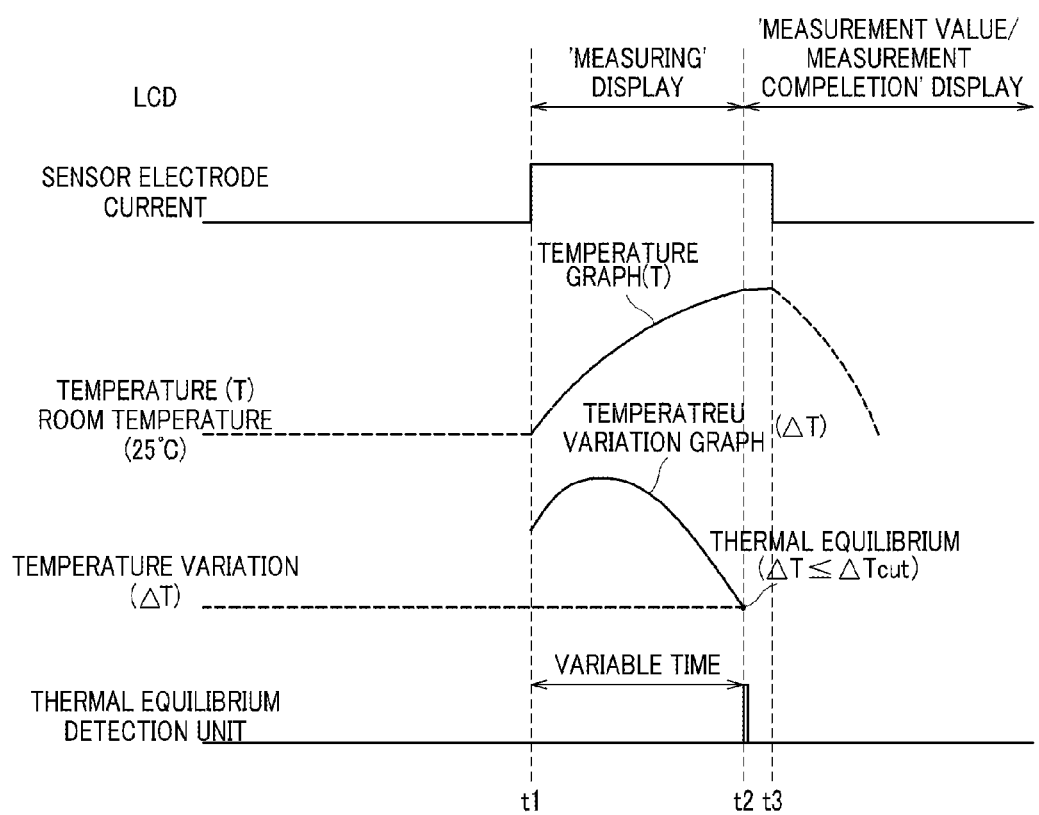
FIG. 4 is a schematic view explaining a measurement principle of an electronic salt meter according to the present invention.

FIG. 4 is a schematic view explaining a measurement principle of an electronic salt meter according to the present invention.

Referring to FIG. 4, when a user throws the sensor rod 110 of the electronic salt meter in the measurement object 20 at a t1 time to measure salinity, current flows between the sensor electrodes 113a and 113b. As a result, the electronic salt meter is automatically turned on to generate vibration for informing a measurement start, and simultaneously, display a letter "measuring" on a liquid crystal display (LCD). Here, the temperature detected by the temperature sensor 118 is significantly increased as shown in the temperature graph T. Also, the vibration for informing the measurement start may be performed one time for a short time to separate it from vibration for informing a measurement completion.

When the measurement starts, a temperature variation ΔT that shows a difference between the current temperature and the previous temperature is significantly increased, and then, is gradually decreased. Thereafter, when the temperature variation ΔT is less than a threshold ΔTcut at a t2 time, the temperature sensor 118 and the measurement object 20 reach thermal equilibrium. At this time, an actual measurement may be performed. Here, according to the present invention, a time until the thermal equilibrium is reached takes approximately 2 seconds to 8 seconds.

When the thermal equilibrium is reached to perform the actual measurement and then the measurement is completed, the measurement completion is expressed through the vibration, and also, a measurement completion icon is displayed on the LCD 130. In addition, a salinity value at an actual temperature is converted into a salinity value at room temperature, and then, the converted salinity is displayed on the LCD 130.

When the measurement is completed, the user draws the sensor rod 110 of the electronic salt meter out the measurement object 20 at a t3 time to confirm a measured value displayed on the LED 130.

Figure 5:
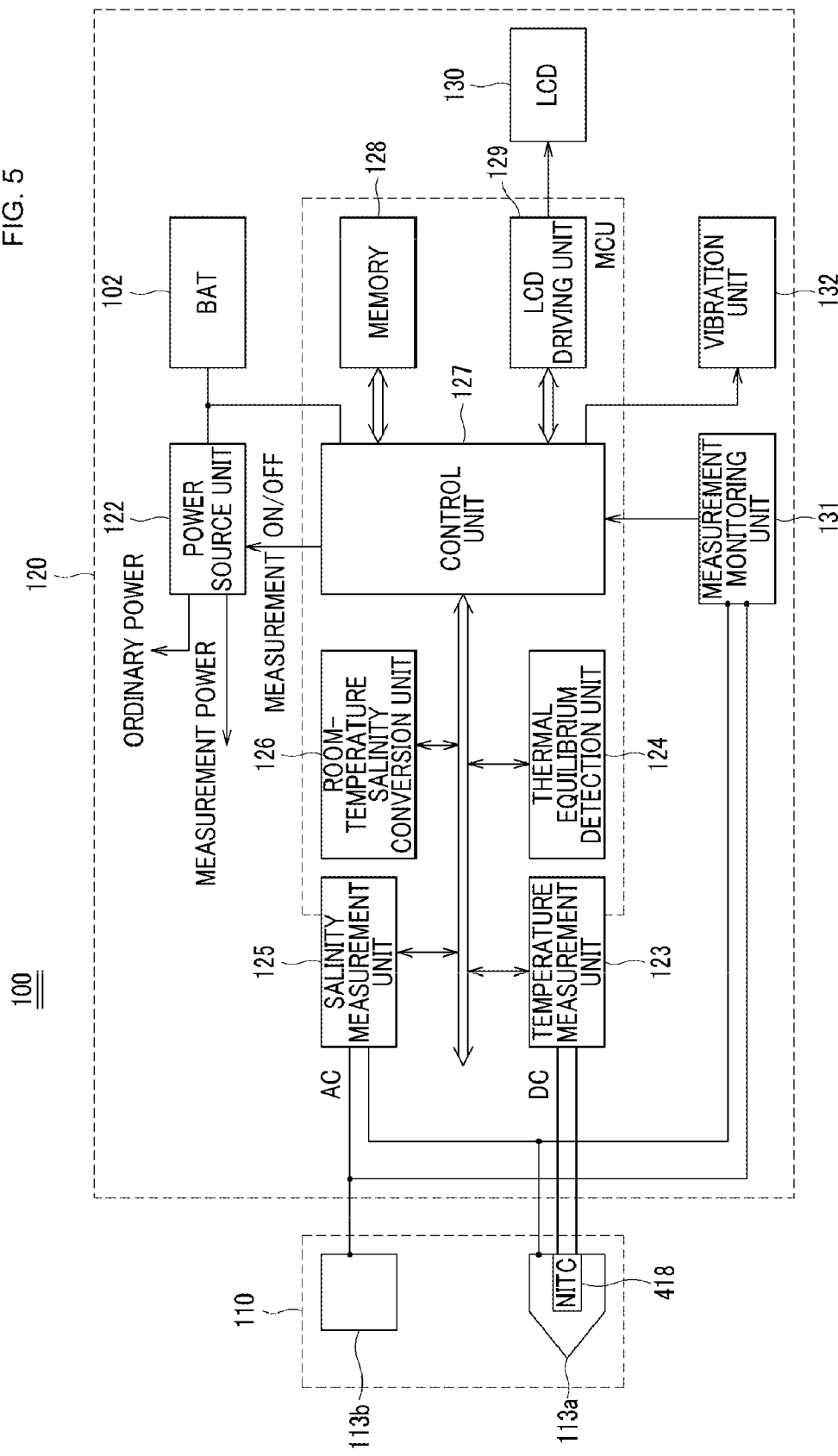
FIG. 5 is a block diagram of an electronic salt meter according to the present invention.

FIG. 5 is a block diagram of an electronic salt meter according to the present invention.

As shown in FIG. 5, according to an electronic salt meter 100 of the present invention, a pair of sensor electrodes 113a and 113b, which are disposed on a sensor rod 110 are connected to a salt meter body 120. A thermistor (NTC) 118 for detecting a heat value of a measurement object 20 is mounted on the first sensor electrode 113a. The salt meter body 120 includes electrical units such as a power source unit 122, a temperature measurement unit 123, a thermal equilibrium detection unit 124, a salinity measurement unit 125, a room-temperature salinity conversion unit 126, a control unit 127, a memory 128, an LCD driving unit 129, an LCD 130, a measurement monitoring unit 131, and a vibration unit 132. Here, a portion of the salinity measurement unit 125, a portion of the temperature measurement unit 123, the room-temperature salinity conversion unit 126, the thermal equilibrium detection unit 124, the control unit 127, the memory 128, and the LCD driving unit 129 may be realized using a single micro controller unit (MCU) including a flash memory and an LCD driving unit and a software.

Referring to FIG. 5, the sensor electrodes 113a and 113b are formed of a metal having good conductivity and heat transmission properties such as platinum-plated copper. Thus, the sensor electrodes 113a and 113b may quickly transmit heat into the built-in thermistor 118. The sensor electrodes 113a and 113b may be connected to the salinity measurement unit 125 to transmit an alternating current (AC) voltage applied by the salinity measurement unit 125 into the measurement object 20, thereby measuring salinity of the measurement object 20 using a conductivity method.

The thermistor 118 is a device in which a resistance thereof is changed according to a temperature. A negative temperature coefficient (NTC) thermistor and a positive temperature coefficient (PTC) thermistor are mainly used as the thermistor 118, and a platinum-plated NTC is mainly used as the temperature sensor. The thermistor 118 is connected to the temperature measurement unit 123 to detect a temperature of the measurement object 20 transmitted through the first sensor electrode 113a.

The measurement monitoring unit 131 monitors whether the sensor electrodes 113a and 113b are electrically connected to each other in a power save mode. Then, when the sensor rod 110 is inserted into the measurement object 20 and the sensor electrodes 113a and 113b are electrically connected to each other, the measurement monitoring unit 131 detects the electrical connection between the sensor electrodes 113a and 113b to inform a measurement start to the control unit 127. Accordingly, the control unit 127 controls the power source unit 122 to output a measurement power, thereby performing an actual measurement. Also, a letter "measuring" is displayed on the LCD 130 during the measurement, and a measured value and a measurement completion icon are displayed on the LCD 130 according to the control of the control unit 127 when the measurement is completed.

The power source unit 122 stabilizes a power applied from a battery 102 to supply an ordinary power into circuit devices. Also, the power source unit 122 supplies the measurement power into the salinity measurement unit 125 when the measurement is turned on according to a measurement ON/OFF control signal of the control unit 127. Here, the ordinary power is a power applied to a minimum number of devices required for the operation in the power save mode. Here, consumption current may be minimized (for example, about 10 μA or less). The measurement power is a power in which the entire circuit devices are normally operated to measure the salinity and temperature of the measurement object.

The temperature measurement unit 123 calculates the current temperature using a detection signal of the NTC temperature sensor 118. The thermal equilibrium detection unit 124 receives and accumulates the measured temperature of the measurement object 20 calculated through the temperature measurement unit 123 to compare 'the currently measured temperature' with 'the previously measured temperature', thereby calculating a temperature variation $\Delta T$. When the temperature variation $\Delta T$ is gradually decreased to reach a predetermined threshold $\Delta Tcut$, it is determined as the thermal equilibrium state to respectively measure the temperature and salinity using the temperature measurement unit 123 and the salinity measurement unit 125.

The salinity measurement unit 125 includes an oscillation circuit that converts the measurement power into an AC power to apply an AC voltage into the sensor electrodes 113a and 113b. Also, the salinity measurement unit 125 calculates conductivity of the measurement object 20 from the current flowing through the sensor electrodes 113a and 113b via the measurement object 20 to measure salinity of the measurement object 20 using the conductivity method.

The room-temperature salinity conversion unit 126 converts the temperature of the measurement object 20 measured by the temperature measurement unit 123 in the thermal equilibrium state and the salinity measured by the salinity measurement unit 125 into a salinity value at room temperature using a transformation formula or a table.

The memory 128 includes a flash memory in which software is stored, a SRAM for storing data, and an EEPROM for storing table values. The control unit 127 executes the software stored in the memory 128 to allow the measurement monitoring unit 131 to detect whether the sensor electrodes 113a and 113b are electrically connected to each other. When the electrical connection between the sensor electrodes 113a and 113b is detected, the control unit 127 controls the power source unit 122 to output the measurement power, thereby performing the actual measurement. During the measurement, a letter "measuring" is displayed on the LCD 130. Also, when thermal equilibrium state is reached, the room-temperature salinity value inputted from the room-temperature salinity conversion unit 126 is displayed on the LCD 130 through the LCD driving unit 129. The LCD 130 may be configured to display operation states such as the letter "measuring", the measurement completion icon, and a low battery icon, or figures for expressing units such as %, ° C., etc, temperature, and salinity according to an operation of the LCD driving unit 129.

The vibration unit 132 is an additional unit for expressing the measurement start and the measurement completion using the vibration according to the control of the control unit 127. The vibration unit 132 is vibrated for a short time when the measurement starts and is vibrated for a long time when the measurement is completed to inform the measurement completion to the user.

FIG. 6 is a flowchart illustrating an operation process of an electronic salt meter 100 according to the present invention.

Referring to FIG. 6, since the electronic salt meter 100 of the present invention does not have separate buttons, an ordinary power for a power save mode is outputted after a battery is inserted. In operations S101 and S102, a measurement monitoring unit 131 operated by the ordinary power monitors whether sensor electrodes 113a and 113b are electrically connected to each other.

When the sensor electrodes 113a and 113b are electrically connected to each other, a control unit 127 expresses 'measurement start' using vibration, and also, a letter 'measuring' is displayed on an LCD 130 without displaying a measured value. Thereafter, a temperature is measured through a temperature measurement unit 123. Then, in operations S103 to S105, a thermal equilibrium detection unit 124 stores the temperature measured by the temperature measurement unit 123, and then compares the current temperature with the previous temperature to calculate a temperature variation $\Delta T$.

Then, the calculated temperature variation $\Delta T$ is compared with a threshold $\Delta Tcut$. As a result, when the temperature variation $\Delta T$ is less than the threshold $\Delta Tcut$, it is determined as the thermal equilibrium state. Thus, in operations S106 and S107, a temperature and salinity of a measurement object are measured through the temperature measurement unit 123 and a salinity measurement unit 125, respectively. Here, the temperature measurement unit 123 may perform temperature compensation to match the detected temperature of an NTC temperature sensor 118 to an actual temperature of the measurement object.

Sequentially, in operation S108, the measured salinity is converted into a salinity value at room temperature using the measured temperature and measured salinity in the thermal equilibrium state. In operations S109 to S111, the salinity value at room temperature and the measurement completion icon are disposed on an LCD 130, and simultaneously, the measurement completion is expressed using vibration to inform the measurement completion to a user. Furthermore, when a preset time (e.g., about 5 minutes) elapses after a power is turned on, a measurement power is automatically turned off and is converted into a power save mode to prevent a battery from being consumed.

According to the electronic salt meter of the present invention, the temperature sensor is built in the sensor electrode disposed on the tip of the sensor rod, and the conductivity is activated by the thermal cream. Also, the heat transmission from the sensor electrode toward a side of the sensor rod may be intercepted (insulated) to quickly obtain the temperature equilibrium between the temperature sensor and the measurement object, thereby quickly measuring the temperature and salinity. For example, although it takes about 2 minutes to measure a temperature in a related art, but it may take about 2 seconds to about 8 seconds to accurately measure the temperature.

Also, according to the electronic salt meter of the present invention, the temperature variation detected by the temperature sensor may be tracked. Thus, when the temperature variation is less than the threshold, it is determined as the thermal equilibrium state. Thus, the temperature and salinity may be measured in the thermal equilibrium state to improve a speed and accuracy of the measurement.

Also, according to the electronic salt meter of the present invention, all manipulation buttons may be removed, and the power may be automatically turned on when the electronic salt meter is thrown into the measurement object. In addition, since 'the measurement start' and 'the measurement completion' are expressed using the vibration or icon, the use convenience may be further improved, and also, the measurement unit may have an effective structure for easily realizing waterproof of water-tight construction.

It will be apparent to those skilled in the art that various modifications and variations can be made in the present invention. Thus, it is intended that the present invention covers the modifications and variations of this invention provided they come within the scope of the appended claims and their equivalents.

What is claimed is:

1. An electronic salt meter comprising:
   a sensor rod configured to easily contact a measurement object;
   a first sensor electrode protruding from a tip of the sensor rod to apply a voltage to the measurement object;
   a second sensor electrode disposed on the tip of the sensor rod to apply the voltage to the measurement object;
   a temperature sensor built in the first sensor electrode to detect a temperature of the measurement object;
   a body case coupled to the sensor rod, the body case having a space in which components are received;
   a power source unit outputting an ordinary power in a power save mode during ordinary times and outputting a measurement power for normally operating a circuit during the measurement;
   a measurement monitoring unit operated by the ordinary power to detect measurement state according to whether the first and second sensor electrodes are electrically connected to each other;
   a salinity measurement unit applying an AC power to the first sensor electrode and the second sensor electrode to measure salinity of the measurement object using a conductivity method;
   a temperature measurement unit applying the power to the temperature sensor to measure the temperature of the measurement object;
   a thermal equilibrium detection unit storing a temperature value previously measured by the temperature measurement unit with a predetermined time interval after the measurement starts according to a control signal and comparing a current temperature with a previous temperature to obtain a temperature variation, and then, when the temperature variation is less than a predetermined threshold, it is determined as a thermal equilibrium state to command actual measurement to the salinity measurement unit and the temperature measurement unit;
   a room-temperature salinity conversion unit converting the salinity value measured by the salinity measurement unit into a salinity value at room temperature using the temperature measured by the temperature measurement unit and the salinity value measured by the salinity measurement;
   a display unit displaying an operation state and the salinity value; and
   a control unit controlling display unit to display a letter 'measuring' on the display unit when the measurement start is detected through the measurement monitoring unit and to receive the salinity value at room temperature from the room-temperature salinity conversion unit, thereby displaying the salinity value at room temperature on the display unit when the thermal equilibrium state is reached while monitoring the thermal equilibrium state through the thermal equilibrium detection unit.

2. The electronic salt meter of claim 1, further comprising a vibration unit expressing measurement start and measurement completion according to the control of the control unit.

3. The electronic salt meter of claim 1, wherein, in the sensor rod, the temperature sensor is disposed in an inner space of the first sensor electrode, a thermal cream for quickly transmitting heat into the temperature sensor is filled within the first sensor electrode, and an insulator having an insulation property is disposed between the first sensor electrode and the second sensor electrode to prevent the heat from being lost toward a rod body, thereby quickly realizing the thermal equilibrium between the temperature sensor and the measurement object.

4. The electronic salt meter of claim 1, wherein the display unit displays a 'measuring' icon of the salinity value and temperature, a 'measurement completion' icon, and a low-voltage state.

5. The electronic salt meter of claim 1, wherein the room-temperature salinity conversion unit converts the salinity value measured by a table showing a relation between the temperature and the salinity into the salinity value at room temperature.

6. The electronic salt meter of claim 1, wherein the temperature measurement unit compensates the temperature measured by the temperature sensor through a compensation table.

* * * * *